(12) United States Patent
Barnes

(10) Patent No.: US 11,737,929 B2
(45) Date of Patent: Aug. 29, 2023

(54) ABSORBENT PAD FOR INTRAVAGINAL USE

(71) Applicant: Stephanie Barnes, Evergreen, CO (US)

(72) Inventor: Stephanie Barnes, Evergreen, CO (US)

( * ) Notice: Subject to any disclaimer, the term of this patent is extended or adjusted under 35 U.S.C. 154(b) by 784 days.

(21) Appl. No.: 16/850,086

(22) Filed: Apr. 16, 2020

(65) Prior Publication Data

US 2021/0322230 A1    Oct. 21, 2021

(51) Int. Cl.
*A61F 13/15* (2006.01)
*A61F 13/20* (2006.01)
*A61F 13/551* (2006.01)
*A61F 13/34* (2006.01)

(52) U.S. Cl.
CPC ...... *A61F 13/15747* (2013.01); *A61F 13/206* (2013.01); *A61F 13/2062* (2013.01); *A61F 13/2094* (2013.01); *A61F 13/34* (2013.01); *A61F 13/55175* (2013.01)

(58) Field of Classification Search
CPC .............. A61F 13/15747; A61F 13/206; A61F 13/2062; A61F 13/2094; A61F 13/34; A61F 13/55175
USPC .................................................... 604/385.17
See application file for complete search history.

(56) References Cited

U.S. PATENT DOCUMENTS

| | | | |
|---|---|---|---|
| 9,566,194 B2 | 2/2017 | Munn | |
| 9,744,081 B2 | 8/2017 | Riordan | |
| 2005/0055003 A1 | 3/2005 | Bittner et al. | |
| 2005/0277904 A1* | 12/2005 | Chase | A61F 13/2065 604/385.18 |

FOREIGN PATENT DOCUMENTS

AU    2006100235 A4    3/2007

* cited by examiner

*Primary Examiner* — Jacqueline F Stephens
(74) *Attorney, Agent, or Firm* — Larry J. Guffey, Esq.; Oliver & Grimsley, LLC

(57) ABSTRACT

An endurance athlete's tampon that eliminates a traditional string and is simpler to manufacture includes a sheet of absorbent material with a bottom edge at whose midpoint there is a downward extending tab, and wherein this tampon is formed by folding it about its lateral centerline that extends upward from the tab so that the sheet's proximal and distal edges are placed proximate one another. This folded sheet is then rolled such that its lateral centerline and tab are at the center of the rolled sheet and its proximal and distal edges are on the outer surface of the rolled sheet. This tab is configured to enable it to be used to remove the tampon after it has been placed in service.

11 Claims, 2 Drawing Sheets

ABSORBENT PAD FOR INTRAVAGINAL USE

BACKGROUND OF THE INVENTION

1. Field of the Invention

The present invention relates generally to surgical articles, and more particularly to an absorbent pad having a specific design and for intravaginal use.

2. Description of the Related Art

Females commonly wear tampons during their menstrual periods to absorb the flow. The tampon commonly used is a super absorbent pad of cotton, rayon, or other material that is rolled or folded into itself to make a generally oblong object fit for being inserted into the vaginal canal. The vaginal wall holds the tampon in place until removed.

Most tampons provide a straight string which extends from the vaginal opening and labia while the tampon is in place inside the vagina. The string provides a mechanism to remove the tampon when needed.

The length and straight nature of the string may be a problem for tampon users. The string may be difficult to grip and pull during tampon removal. Thus, the string has to be fairly long to allow the fingers to get a solid grip on the string before pulling to remove the tampon. Because it is so long, the string can hang out of bathing suits or underwear or may get in the way of the urine stream. Additionally, it can be a problem for endurance athletes when strings of an excessive length can lead to chafing.

Additionally, using a string for a tampon's removal adds to the complexity and expensive of a tampon's fabrication because the appropriate string is effectively another raw material that a tampon manufacturer must acquire and work with as the manufacturer attaches it to an absorbent pad.

There have been prior efforts to construct a tampon without a straight string attached to an absorbent pad. See, for example, U.S. Patent Publication Number 2005/0055003, U.S. Pat. Nos. 9,566,194 and 9,744,081 and Australian Patent No. 2006/100235. However, there are apparently still problems with these alternative designs since none of them seem to have established any sort of a presence in the worldwide market for tampons.

Despite this prior art, there continues to be a need for improved tampons that are easier to use in certain situations (e.g., when wearing a bathing suit) and which can also be manufactured by using simpler fabrication methods.

SUMMARY OF THE INVENTION

Recognizing the need for the development of improved tampons that are easier to use in certain situations (e.g., when wearing a bathing suit) and which can also be manufactured by using simpler fabrication methods, the present invention seeks to provide such an improved tampon.

In accordance with a preferred embodiment of the present invention, an endurance athlete's tampon, that eliminates a traditional string and is simpler to manufacture, includes a sheet of absorbent material with a bottom edge at whose midpoint there is a downward extending tab, and wherein this tampon is formed by folding it about its lateral centerline that extends upward from the tab so that the sheet's proximal and distal edges are placed proximate one another. This folded sheet is then rolled such that its lateral centerline and tab are at the center of the rolled sheet and its proximal and distal edges are on the outer surface of the rolled sheet. Additionally, this tab is configured to enable it to be used to remove the tampon after it has been placed in service.

In accordance with another preferred embodiment of the present invention, the tampon of the present invention includes a cylindrical, elongate body having a bottom edge and wherein this body is fabricated from an absorbent material. A tab extends from the body's bottom edge and this tab is also fabricated from the same absorbent material. Furthermore, this tab is configured so that it can be grasped by a tampon user and used to remove the tampon after it has been placed in service.

In accordance with yet another preferred embodiment of the present invention, it takes the form of a method of forming a tampon that includes the steps of: (1) providing a sheet of absorbent material having right-side and left-side surfaces, top, bottom, proximal and distal edges, (2) wherein this bottom edge has a proximal and a distal end and a midpoint therebetween and a tab that extends downward from this midpoint, (3) wherein this top surface has a lateral centerline that is located proximate the bottom edge's midpoint and extends between the top and bottom edges, (4) initially forming the tampon by folding the sheet about its lateral centerline so that its proximal and distal edges are placed proximate one another, (5) then rolling this folded sheet to form a rolled, folded sheet which has an outer surface and wherein the lateral centerline and tab are at the center of this rolled, folded sheet and its proximal and distal edges are on the outer surface of the rolled, folded sheet, and (6) configuring the to enable it to be used to remove the tampon after it has been placed in service.

Thus, there has been summarized above (rather broadly and understanding that there are other preferred embodiments which have not been summarized above) the present invention in order that the detailed description that follows may be better understood and appreciated.

DESCRIPTION OF THE PREFERRED EMBODIMENT

Figure 1A:
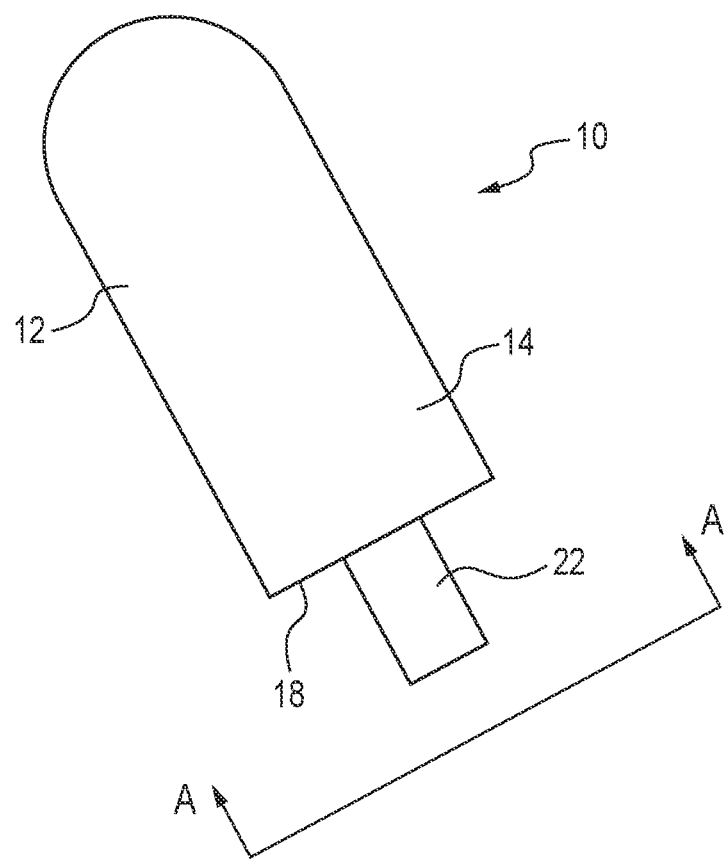
FIG. 1A is a perspective view of a preferred embodiment of the present invention in the form of an absorbent pad/elongated body for intravaginal use, or a tampon.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Figure 1B:
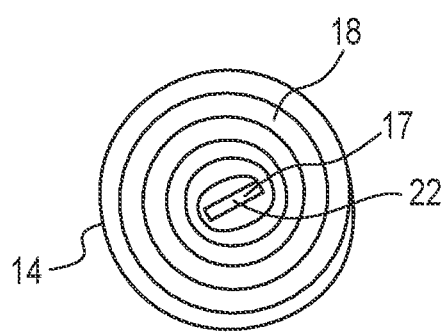
FIG. 1B is a bottom end view of the preferred embodiment of the present invention shown in FIG. 1A.

Referring to FIG. 1, there is illustrated a perspective view of a preferred embodiment of the present invention 10. In this embodiment, the present invention takes the form of a cylindrical, elongate body 12 or tampon that has an outer or peripheral surface 14 and, top 16 and bottom 18 edges, and a center 17. It has been formed by rolling or folding together the exterior surface 25 of a single sheet 20 of absorbent material to form a generally oblong shape. From the body's bottom edge there is seen to extend a ribbon-shaped, tongue or tab 22. To ensure that this body remains rolled or folded, it may be sewn or glued or attached together by other means known in the art of tampon manufacturing.

The length of the elongated body's tab may extend, as desired, any distance from the body's bottom edge. For example, this tab 22 may extend greater than one inch or less than one inch from the body's bottom edge 18. Preferably, the tab will extend far enough from the bottom edge of the elongate body to cross the vaginal wall of one who is using this tampon and reach the outside of the vaginal opening, such that it rests inside the user's garment.

With the length of this tab being defined as the distance the tip 23 of the tab extends from the bottom edge 18 of the elongate body. Preferred lengths of this tab are in the range of 0.5-1.5 inches and 1.5-3.0 inches. For endurance athletic events (e.g., long distance running), a preferred length of the tab has been found to be approximately 1.0 inch.

In operation, this tampon 12 may be used with any applicators (not shown) known in the art to assist in inserting the tampon into a vagina. The top edge 16 of the tampon is inserted first into the vagina allowing the bottom edge 18 of the tampon to be closest the vaginal opening.

To remove the tampon, the tab 22 may be gripped or grasped by a user's fingers to allow the tampon to be pulled from the user's vagina and discarded.

The elongate body 12 is made from an absorbent material typically used in the art for making tampons, such as cotton or rayon. The absorbent material may be hydrophilic (affinity to absorb fluids) on its top edge 16 and hydrophobic (resistant to water or fluid absorption) on its bottom edge 18. In this manner, the tampon will absorb fluids within the vagina and prevent fluids from entering the tampon from outside of the vagina, such as water from a swimming pool.

Figure 2:
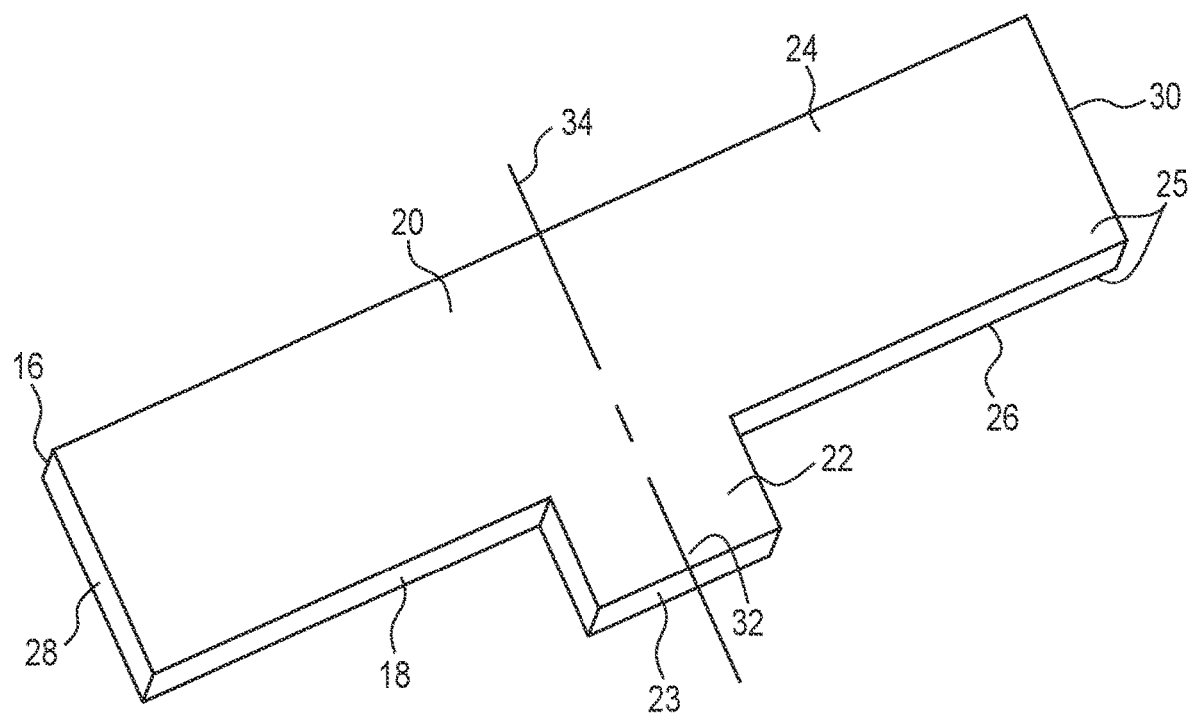
FIG. 2 a perspective view of an essentially flat sheet of absorbent material from which the present tampon is formed.

Shown in FIG. 2 a perspective view of an essentially flat sheet 20 of absorbent material from which the present tampon is formed. It is seen to have right-side 24 and left-side 26 surfaces, top 16, bottom 18, proximal 28 and distal 30 edges.

The bottom edge 18 is seen to have a midpoint 32 from which downwardly extends a tongue or tab 22. A lateral centerline 34 is defined to pass thru this midpoint and extend between these top and bottom edges.

Figure 3:
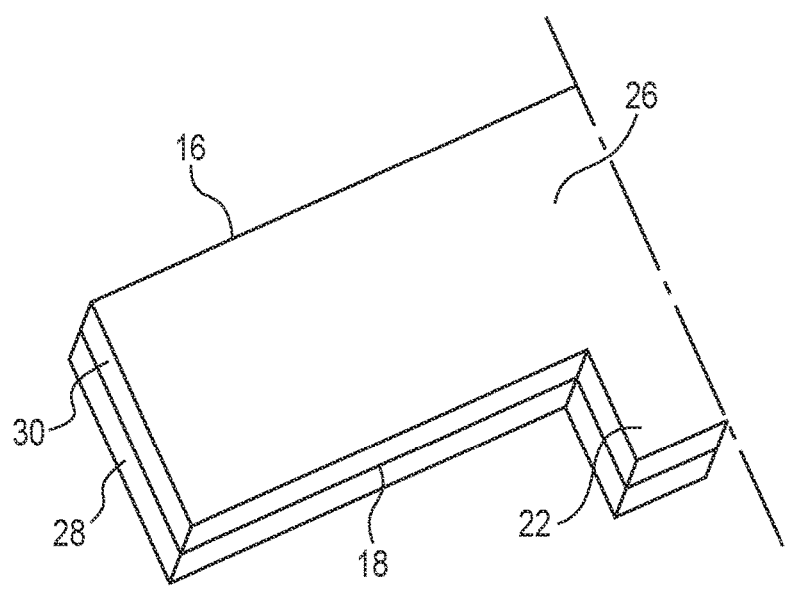
FIG. 3 a perspective view of the flat sheet of FIG. 2 after it has been initially folded about its lateral centerline so that its proximal and distal edges are placed proximate one another.

The tampon is initially formed by folding this sheet about its lateral centerline 34 so that its proximal 28 and distal 30 edges are placed proximate one another. See FIG. 3. It is then further formed by rolling or folding this initially folded sheet so as to form a substantially solid generally cylindrical shape which has its lateral centerline and tongue or tab 22 at the center of the resulting cylindrical, elongated body and the sheet's proximal and distal edges are on the outer surface 14 of the elongated body. As previously noted, the tongue or tab 22 is configured to a desired length and shape to form a means that is used to remove the tampon after it has been placed in service.

The foregoing is considered as illustrative only of the principles of the present invention. Further, since numerous modifications and changes will readily occur to those skilled in the art, it is not desired to limit the invention to the exact construction and operation shown and described herein. Accordingly, all suitable modifications and equivalents may be resorted to, falling within the scope of the invention that is hereinafter set forth in the claims to the invention.

I claim:

1. A tampon comprising:
   a cylindrical, elongate body having a bottom edge, a peripheral surface and a center,
   wherein said body is fabricated from a single sheet of an absorbent material that has an exterior surface,
   wherein said peripheral surface is formed from a portion of said sheet exterior surface,
   a tab extending from said bottom edge,
   wherein said tab is also fabricated from said sheet.

2. The tampon as recited in claim 1, wherein:
   said tab is configured so that said tab can be grasped by a tampon user and used to remove said tampon after it has been placed in service.

3. The tampon as recited in claim 2, wherein:
   said sheet has proximal and distal edges and said bottom edge of said sheet includes a midpoint and a lateral centerline that extends through said midpoint,
   said tab extends downwardly from said midpoint,
   said tampon is initially formed by folding said sheet about said lateral centerline so that said proximal and distal edges of said sheet are placed proximate one another to yield a folded sheet of absorbent material, and
   said folded sheet is rolled such that said lateral centerline and tab are at said center of the resulting rolled sheet which assumes the shape of said cylindrical, elongated body.

4. The tampon as recited in claim 3, wherein:
   said tab has a tip and the distance between said tip and said bottom edge defines the length of said tab, and
   said length of said tab has a preferred range of 0.5-1.5 inches.

5. The tampon as recited in claim 3, wherein:
   said tab has a tip and the distance between said tip and said bottom edge defines the length of said tab, and
   said length of said tab has a preferred range of 1.5-3.0 inches.

6. The tampon as recited in claim 2, wherein:
   said sheet has proximal and distal edges and said bottom edge of said sheet includes a midpoint and a lateral centerline that extends through said midpoint,
   said tab extends downwardly from said midpoint,
   said tampon is initially formed by folding said sheet about said lateral centerline so that said proximal and distal edges of said sheet are placed proximate one another to yield a folded sheet of absorbent material, and
   said folded sheet is folded such that said lateral centerline and tab are at said center of the resulting folded sheet which assumes the shape of said cylindrical, elongated body.

7. The tampon as recited in claim 1, wherein:
   said sheet has proximal and distal edges and said bottom edge of said sheet includes a midpoint and a lateral centerline that extends through said midpoint,
   said tab extends downwardly from said midpoint,
   said tampon is initially formed by folding said sheet about said lateral centerline so that said proximal and distal edges of said sheet are placed proximate one another to yield a folded sheet of absorbent material, and
   said folded sheet is rolled such that said lateral centerline and tab are at said center of the resulting rolled sheet which assumes the shape of said cylindrical, elongated body.

8. The tampon as recited in claim 1, wherein:
said sheet has proximal and distal edges and said bottom edge of said sheet includes a midpoint and a lateral centerline that extends through said midpoint,
said tab extends downwardly from said midpoint,
said tampon is initially formed by folding said sheet about said lateral centerline so that said proximal and distal edges of said sheet are placed proximate one another to yield a folded sheet of absorbent material, and
said folded sheet is folded such that said lateral centerline and tab are at said center of the resulting folded sheet which assumes the shape of said cylindrical, elongated body.

9. The method of forming a tampon, said method comprising the steps of:
providing a sheet of absorbent material having right-side and left-side surfaces, top, bottom, proximal and distal edges,
wherein said bottom edge having a proximal and a distal end and a midpoint therebetween and a tab that extends downward from said midpoint,
wherein said top surface having a lateral centerline that is located proximate said bottom edge midpoint and extends between said top and bottom edges,
initially forming said tampon by folding said sheet about said lateral centerline so that said proximal and distal edges are placed proximate one another,
further forming said tampon by rolling said folded sheet to form a rolled, folded sheet which has an outer surface and wherein said lateral centerline and tab are at the center of said rolled, folded sheet and said proximal and distal edges are on said outer surface of said rolled, folded sheet, and
configuring said tab to enable said tab to be used to remove said tampon after it has been placed in service.

10. The method of forming a tampon as recited in claim 9, wherein:
said tab has a tip and the distance between said tip and said bottom edge defines the length of said tab, and
said length of said tab has a preferred range of 0.5-1.5 inches.

11. The method of forming a tampon as recited in claim 9, wherein:
said tab has a tip and the distance between said tip and said bottom edge defines the length of said tab, and
said length of said tab has a preferred range of 1.5-3.0 inches.

* * * * *